(12) United States Patent
Wack et al.

(10) Patent No.: US 8,917,432 B2
(45) Date of Patent: Dec. 23, 2014

(54) MULTIPLEXING EUV SOURCES IN RETICLE INSPECTION

(75) Inventors: Daniel Wack, Fredericksburg, VA (US); Daimian Wang, Fremont, CA (US); Karl R. Umstadter, Livermore, CA (US); Ed Ma, Alameda, CA (US); Frank Chilese, San Ramon, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 241 days.

(21) Appl. No.: 13/563,850

(22) Filed: Aug. 1, 2012

(65) Prior Publication Data

US 2014/0036333 A1 Feb. 6, 2014

Related U.S. Application Data

(60) Provisional application No. 61/621,704, filed on Apr. 9, 2012.

(51) Int. Cl.
*G02B 26/08* (2006.01)
*G03F 7/20* (2006.01)
*G02B 26/12* (2006.01)

(52) U.S. Cl.
CPC ............ *G02B 26/123* (2013.01); *G03F 7/7005* (2013.01)
USPC .................. 359/204.1; 359/203.1; 359/216.1; 250/504 R (58) Field of Classification Search
CPC . G02B 26/123; G01N 21/8806; G01N 21/95; G01N 21/956; G01N 21/9501; G01N 21/33; G03F 1/84; G03F 7/20; G03F 7/70; G03F 7/70041; G03F 7/7005; G03F 7/70058; G03F 7/70066; G03F 7/70075; G03F 7/702; G03F 7/70208; G03F 7/00; G03F 7/70616
USPC ............. 359/216.1–219.2, 204.1–204.5, 855; 250/492.1, 492.3, 504 R; 355/67, 70; 356/237.1, 237.2, 237.5; 378/34
See application file for complete search history.

(56) References Cited

U.S. PATENT DOCUMENTS

| | | | |
|---|---|---|---|
| 5,617,133 A | 4/1997 | Fisli | |
| 5,898,492 A | 4/1999 | Imaino et al. | |
| 5,981,944 A | 11/1999 | Ito | |
| 6,568,811 B2 * | 5/2003 | Noda et al. | 353/31 |
| 2006/0072191 A1 | 4/2006 | Akiyama et al. | |
| 2007/0181834 A1 * | 8/2007 | Kleinschmidt | 250/504 R |
| 2007/0295919 A1 | 12/2007 | Endres et al. | |

* cited by examiner

*Primary Examiner* — James Phan
(74) *Attorney, Agent, or Firm* — Suiter Swantz pc llo (57) ABSTRACT

The present disclosure is directed to an illumination system. The illumination system may include a base member rotatable about a rotation axis and a plurality of mirrors disposed on an outer surface of the base member along a perimeter of the base member. The mirrors may be oriented at a predetermined angle. The illumination system also includes at least two illumination sources. Each of the mirrors of the first plurality of mirrors is configured to receive radiation from the first illumination source at a first portion of each mirror at a first time. The mirror is configured to reflect the radiation to an optical path. Each of the mirrors is further configured to receive radiation from the second illumination source at a second portion of the mirror at a second time. The mirrors reflect the radiation from the second illumination source to the common optical path.

19 Claims, 12 Drawing Sheets

MULTIPLEXING EUV SOURCES IN RETICLE INSPECTION

CROSS-REFERENCE TO RELATED APPLICATION

The present application is related to co-pending U.S. patent application Ser. No. 13/419,157 filed on Mar. 13, 2012 and entitled "SOURCE MULTIPLEXING ILLUMINATION FOR MASK INSPECTION," which is incorporated herein by reference.

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)) For purposes of the USPTO extra-statutory requirements, the present application constitutes a regular (non-provisional) patent application of United States Provisional patent application entitled MULTIPLEXING EUV SOURCES IN EUV RETICLE INSPECTION TOOL, naming Dan Wack, Frank Chilese, Ed Ma, Daimian Wang, Karl Umstadter as inventors, filed Apr. 9, 2012, Application Ser. No. 61/621,704.

TECHNICAL FIELD

The disclosure generally relates to the field of reticle inspection, and particularly to methods and systems for providing source multiplexing illumination for reticle inspection.

BACKGROUND

Reticle inspection is an operation of checking the correctness of a reticle which is used for generating a pattern for transferring onto a substrate (for example, in semiconductor device fabrications). Modern technologies for locating defects in reticles are automated systems that involve scanning electron microscopy and other advanced tools. Existing illumination systems in the market for reticle inspection employ ultra-violet light at or above 193 nm that are not sufficient to resolve the features and defects below the 22 nm node. In order to resolve features and defects below 22 nm node, light of shorter wavelength in the EUV (e.g., 13.5 nm) region needs to be used. Since the brightness of commercially available EUV sources are not sufficient, multiple sources are required.

There are several existing illumination techniques for supporting multiple sources. One such technique is disclosed in U.S. Pat. No. 6,396,068, which uses a two-stage method to increase the number of source units that can be temporally multiplexed. According to this technique, multiple sources are placed on translational stages that select different sources at different times. A rotational stage acts as a beam combiner that selects beams from several sources selected in the first stage. However, this technique can only multiplex a few source units within a limited track length (e.g., 2-3 m from a commercially available EUV source to mask) and small range of normal or grazing incident angles where mirror reflectivity is high (R>60% for 0-20° normal incidence, and R>80% for 0-15° grazing incidence). In addition, the reflected optical path changes its direction due to the duration of each pulse, the sources time jitter (pulses are emitted at different times than expected), and the rotatable or translational base is subject to velocity instability.

Another technique is disclosed in U.S. Pat. No. 6,861,656, which selectively tilts a planar mirror angle in coordinates with a selective activation of EUV source units. However, this technique also can only multiplex a few source units within a limited track length. Furthermore, the reflected optical path also changes its direction based on the duration of each pulse, the sources time jitter, and the rotatable or translational base is subject to velocity instability.

Still another technique is disclosed in U.S. Pat. No. 7,183,565, which uses a rotatable base to reflect EUV beams from multiple sources. The rotatable base comprises multiple mirrors mounted at various angles and displaced radially from the axis of rotation. The mirrors are positioned to reflect light in the near normal incident direction. However, this technique also has the same shortcomings as the other techniques described above.

A further technique is disclosed in U.S. patent application Ser. No. 11/622,241, which uses a reflecting optical element that is mounted to a step or servo rotatable motor to reflect multiple EUV sources to a common optical path for use in semiconductor lithography. This technique can only multiplex a few source units within a limited track length.

Therein lies a need for a method and apparatus for delivering EUV photons from multiple sources to an EUV reticle inspection tool, without the aforementioned shortcomings.

SUMMARY

The present disclosure is directed to an illumination system. The illumination system may include a base member rotatable about a rotation axis and a plurality of mirrors disposed on an outer surface of the base member along a perimeter of the base member. The mirrors may be oriented at a predetermined angle. The illumination system also includes at least two illumination sources. Each of the mirrors of the first plurality of mirrors is configured to receive radiation from the first illumination source at a first portion of each mirror at a first time. The mirror is configured to reflect the radiation to an optical path. Each of the mirrors is further configured to receive radiation from the second illumination source at a second portion of the mirror at a second time. The mirrors reflect the radiation from the second illumination source to the common optical path.

A further embodiment of the invention is also directed to an illumination system. The illumination system may include a base member rotatable about a rotation axis, a first plurality of mirrors disposed on an outer surface of the base member along a perimeter of the base member and oriented at a predetermined angle. The illumination system may further comprise a second plurality of mirrors disposed on an outer surface of the base member along a perimeter of the base member and oriented at a second predetermined angle. Each mirror of the first plurality of mirrors may be interleaved with each mirror of the second plurality of mirrors. The illumination system may also include four different illumination sources. A mirror of the first plurality of mirrors is configured for receiving radiation from the first illumination source at a first portion of the mirror at a first time and reflecting the radiation to an optical path, and the same mirror of the first plurality of mirrors is configured for receiving radiation from the second illumination source at a second portion of the mirror at a second time and reflecting the radiation to the optical path, the first portion being different from the second portion. A mirror of the second plurality of mirrors may also be configured for receiving radiation from the third illumination source at a first portion of the mirror at a third time and reflecting the radiation to an optical path and the same mirror of the second plurality of mirrors is configured for receiving radiation from the fourth illumination source at a second portion of the mirror at a fourth time and reflecting the radiation to the optical path, the first portion being different from the second portion.

A further embodiment of the invention is directed to a method of reflecting radiation from a plurality of illumination sources to a common optical path. The method includes the steps of providing a first plurality of mirrors disposed on a rotatable base member and receiving radiation from a first illumination source at a first portion of a first mirror of the first plurality of mirrors at a first time. A further step of the method involves reflecting the radiation from the first illumination source to an optical path. A further step involves rotating the base member about a rotation axis, and then receiving radiation from a second illumination source at a second portion of the first mirror of the first plurality of mirrors at a second time. The final step is reflecting the radiation from the second illumination source to the optical path.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

The present disclosure is directed to methods and systems for delivering extreme ultraviolet (EUV) photons from multiple sources to an EUV reticle inspection tool. Existing EUV sources fail to provide adequate brightness for reticle inspection. In accordance with the present disclosure, multiple pulsed EUV sources are multiplexed to increase the total source brightness.

Figure 1:
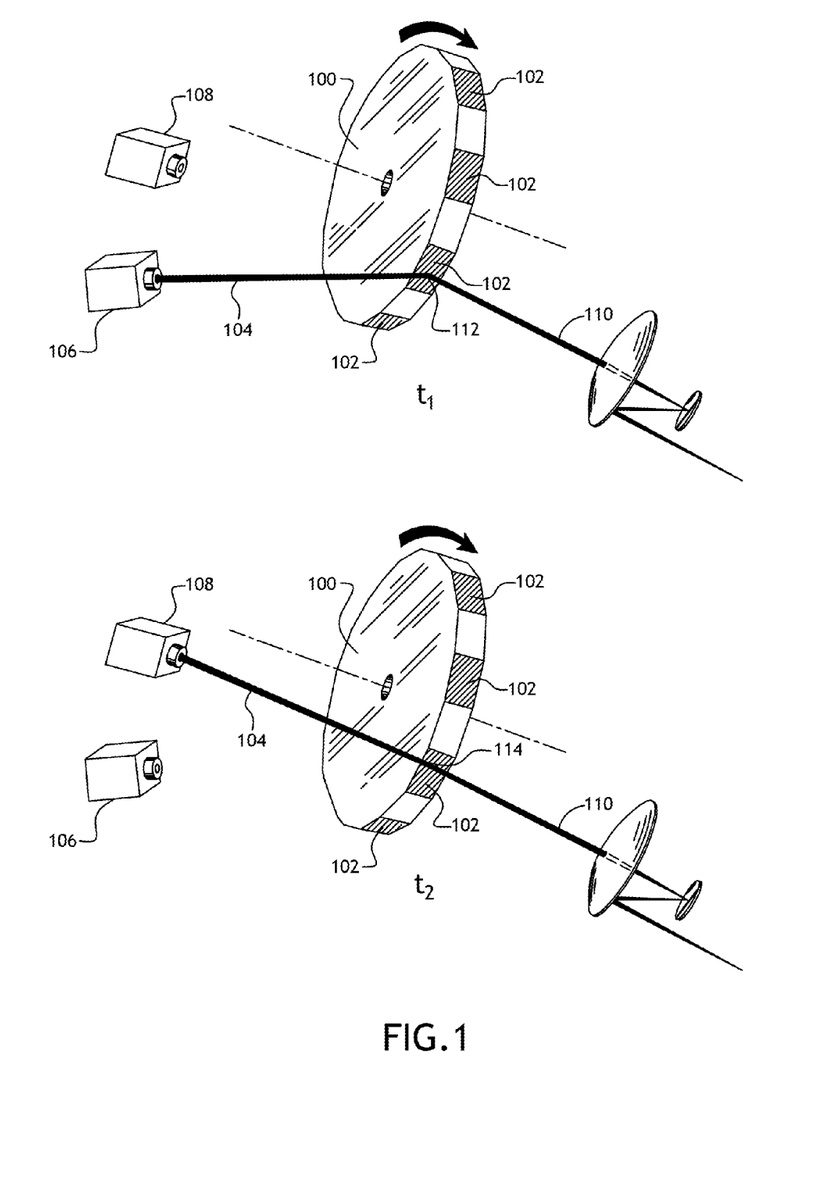
FIG. 1 is an isometric view of an illumination system at a first time instance and a second time instance.

Referring to FIG. 1, one embodiment of the illumination system in accordance to the present disclosure is shown. The illumination system may include a rotatable base member 100 rotatable about a rotation axis. The base member 100 may provide surfaces where mirrors may be mounted. For instance, a plurality of mirrors 102 may be mounted to the perimeter of the base member 100. In this manner, radiation 104 from a first illumination source 106 and radiation 104 from a second illumination source 108 may be received by the mirrors 102 and reflected to a common optical path 110. The mirror surface of each one of the plurality of mirrors 102 is positioned to generally face away from the rotation axis (i.e., the mirrors 102 face outwards). In addition, the mirror surface of each one of the plurality of mirrors 102 is oriented on the base member 100 at a first predetermined angle α. Such a configuration allows each mirror of the plurality of mirrors 102 to reflect radiation from a first illumination source 106 to the common optical path 110 each time that the particular mirror rotates past the first illumination source 106 at a specified point.

The plurality of mirrors 102 are also configured to receive radiation from a second illumination source 108 and reflect it to the same common optical path 110 as the radiation from the first illumination source 106. In one embodiment of the invention, each mirror of the plurality of mirrors is configured to receive radiation from the first illumination source 106 at a first portion 112 at a first time instance ($t_1$) and reflect the radiation to the optical path 110, as shown in FIG. 1. The base member 100 then rotates a predetermined amount, and the same mirror receives radiation from the second illumination source 108 at a second portion 114 at a second time instance ($t_2$) and reflects the radiation to the optical path 110. The rotation of the base member 100 may be continuous during the timeframe when the mirrors are receiving and reflecting radiation to the common optical path 110.

It is contemplated that the number of mirrors included on the base member 100 is determined based on the rotation speed of the base member 100 and the pulse rate of the corresponding illumination source. For instance, each time the first illumination source emits radiation, one of the plurality of mirrors 102 may be rotated in place for reflecting the emission from the first illumination source 106. Similarly, each time the second illumination source 108 emits radiation, the same mirror from the plurality of mirrors 102 needs to be rotated in place for reflecting the emission from the second illumination source 108 at a portion of the mirror 114 distinct from the location of reflection of the first light source 106. The rotation of the base member 100 may be continuous during the timeframe when the mirrors are receiving and reflecting radiation to the common optical path 110, with the rotation speed calibrated to facilitate the proper alignment of illumination sources and mirrors to receive and reflect the radiation to the common optical path 110.

It is also contemplated that additional illumination sources may be positioned near the first illumination source or the second illumination source. For example, a third, fourth, fifth, and sixth illumination source may be positioned near the first and second illumination source. The additional illumination sources may emit radiation onto a particular mirror of the plurality of mirrors at a third, fourth, fifth, and sixth portion of the particular mirror. The mirror will reflect the radiation from each of the illumination sources to the same common optical path. This configuration allows the base member to be utilized for reflecting radiation from multiple illumination sources to the common optical path.

It is also contemplated that additional illumination sources may be positioned near the first illumination source or the second illumination source. The additional illumination sources may correspond to a second plurality of mirrors mounted to the base member. This additional set of mirrors may interleave with a first plurality of mirrors, and this configuration allows the base member to be utilized for reflecting radiation from multiple sets of illumination sources to the common optical path.

Figure 2A:
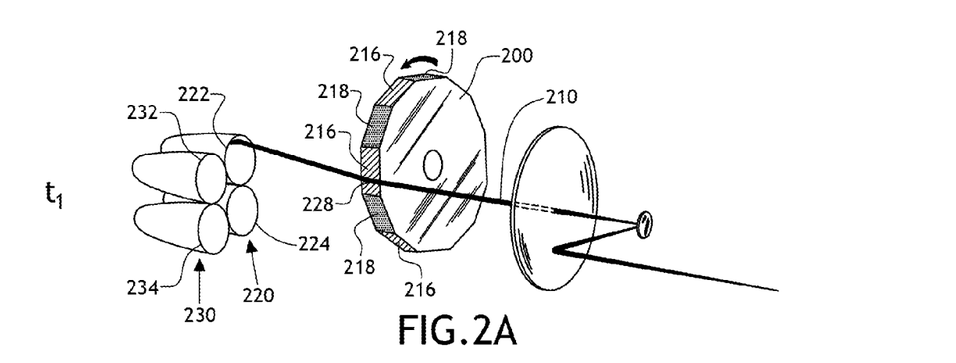
FIGS. 2A through 2D show an isometric view of an illumination system at a first, second, third, and fourth time instance.
Figure 2B:
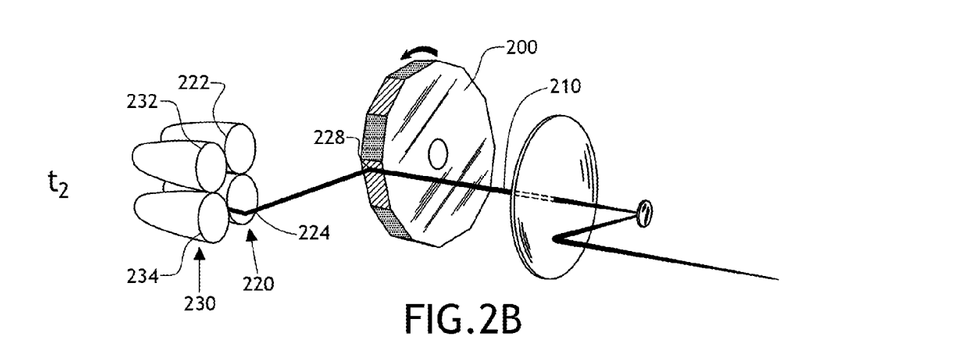
Figure 2C:
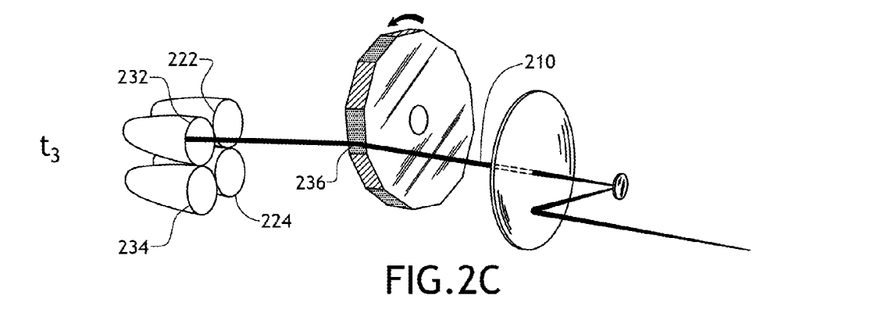
Figure 2D:
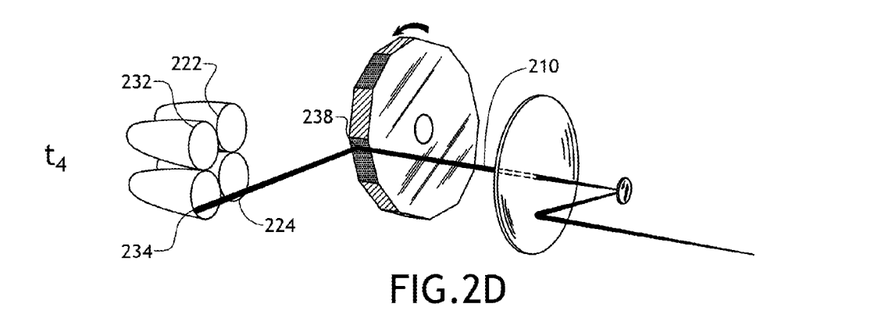
Figure 3A:
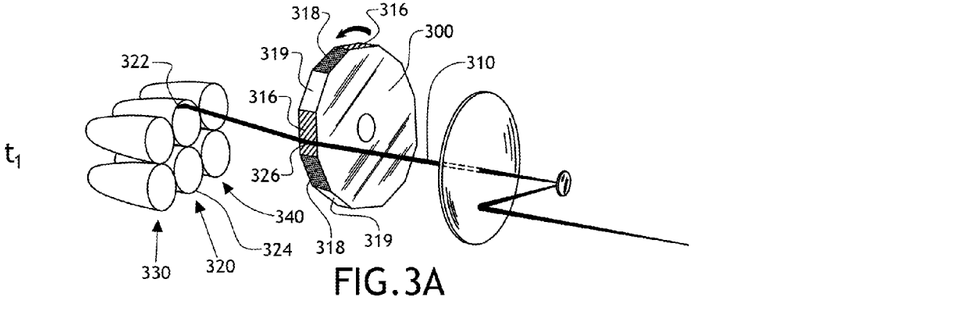
FIGS. 3A through 3F show an isometric view of an illumination system at a first, second, third, fourth, fifth, and sixth time instance.
Figure 3B:
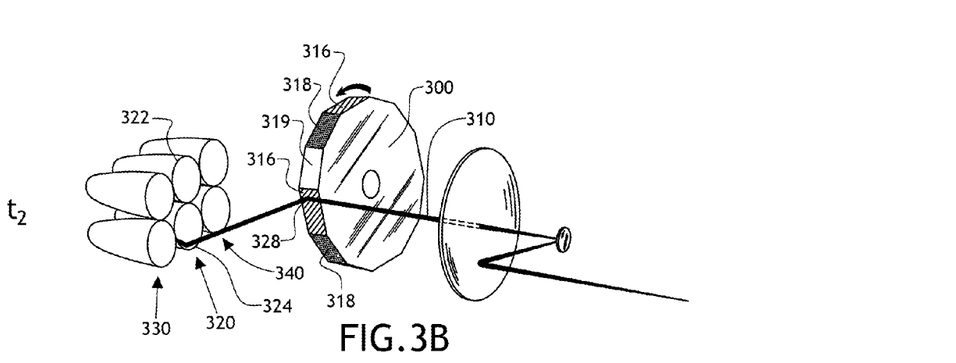
Figure 3C:
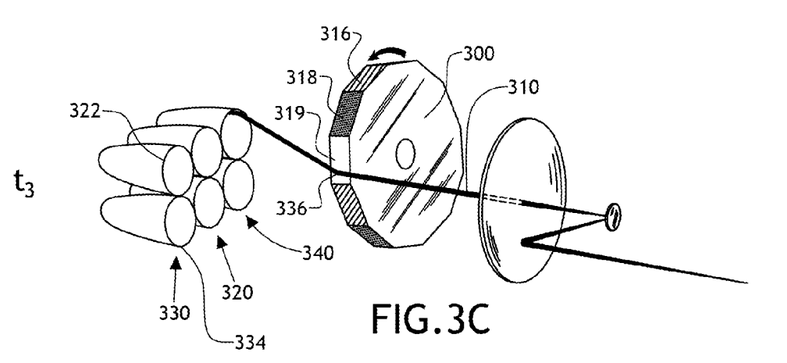
Figure 3D:
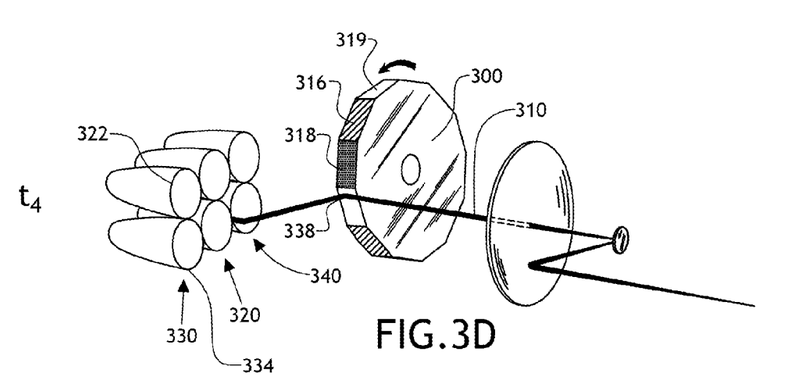
Figure 3E:
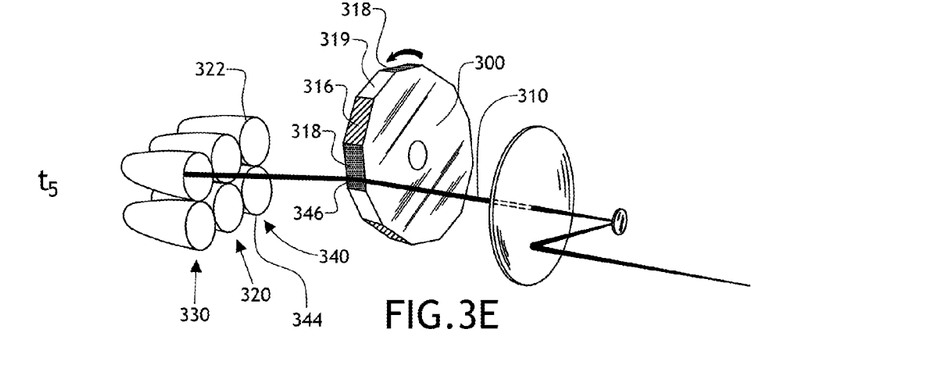
Figure 3F:
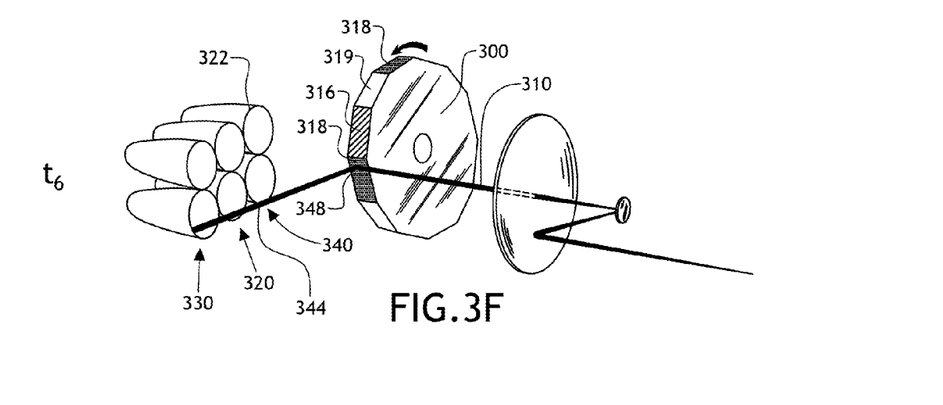

FIGS. 2A through 2D illustrate an illumination system including two pluralities of mirrors for reflecting multiple illumination sources to the common optical path, in accordance with one embodiment of the present invention. A base member 200 may include a first set of mirrors 216 interleaved with a second set of mirrors 218 as shown in FIG. 2A. In such a configuration, the first and second set of mirrors are positioned to generally face away from the rotation axis of the base member 200. In addition, the mirror surface of each one of the second set of mirrors 118 is oriented on the base member 200 at a second predetermined angle θ. A first set of illumination sources 220, comprising a first illumination source 222 and a second illumination source 224, are positioned to emit radiation that will strike each face of the first set of mirrors 216 at a first portion 226 and a second portion 228.

For example, a particular mirror from the first set of mirrors 116 receives the radiation from the first illumination source 222 at a first portion 226 of the mirror at a first time instance ($t_1$) and reflects the radiation to the optical path 210. The base member 200 then rotates a predetermined amount, and the same mirror receives radiation from the second illumination source 224 at a second portion 228 of the mirror at a second time instance ($t_2$) and reflects the radiation to the optical path 210. The illumination system may further comprise a second set of illumination sources 230, comprised of a third illumination source 232 and a fourth illumination source 234. A particular mirror of the second set of mirrors 118 reflects radiation from the third source 232 at a first portion 236 of the particular mirror at a third time instance ($t_3$) and reflects the radiation to the optical path 210. The base member 200 then rotates a predetermined amount, and the same mirror receives radiation from the fourth illumination source 234 at a second portion 238 of the mirror at a fourth time instance ($t_4$) and reflects the radiation to the optical path 210.

It is also contemplated that the illumination system may be expanded to accommodate additional illumination sources. In an alternative embodiment of the invention, a total of six illumination sources may be multiplexed to a common optical path. A third set of illumination sources may be positioned near the first set of illumination sources or the second set of illumination sources, as depicted in FIGS. 3A through 3F. The third set of illumination sources 340 may correspond to a third set of mirrors 319 mounted to the outer surface of the base member 300. The third set of mirrors 319 may interleave with the first set of mirrors 316 and the second set of mirrors 318, and this configuration allows the base member 300 to be utilized for reflecting radiation from at least three sets of two illumination sources to the common optical path 310.

FIGS. 3A through 3F illustrate how the base member 300 may reflect radiation from a first 320, second 330, and third 340 set of sources to a common optical path 310. A particular mirror from the first set of mirrors 316 receives the radiation from the first source 320 at a first portion 326 of the mirror at a first time instance ($t_1$) and reflects the radiation to the optical path 310. The base member 300 then rotates a predetermined amount, and the same mirror 316 receives radiation from the second illumination source 324 at a second portion 328 of the mirror at a second time instance ($t_2$) and reflects the radiation to the optical path 310. This process repeats for each illumination source of each set of illumination sources and their respective corresponding set of mirrors.

It is contemplated that the number of sets of mirrors is determined based on the rotation speed of the base member, the pulse rate of the corresponding light source, and the total number of illumination sources. Each of the mirrors must be oriented to receive the emission from a corresponding set of light sources on at least two locations on the mirror surface. In the embodiments depicted in FIGS. 1, 2A through 2D, and 3A through 3F, each mirror reflects radiation from at least two sources to the common optical path from two different locations on the mirror surface. However, it is contemplated that the each particular mirror could reflect radiation from more than two sources to the common optical path. In such an instance, each source would contact the mirror at a different portion and time instance and reflect the radiation to the common optical path.

By utilizing two different locations on each of the mirrors to reflect radiation from more than one source, the number of illumination sources that can be temporally multiplexed increases without requiring a larger base member. In one configuration, the sources are arranged in rows of two, with each set of sources corresponding to a set of mirrors on the base member. However, it is contemplated that the specific number and arrangement of sources provided from each direction may vary without departing from the spirit and scope of the present disclosure.

Figure 4:
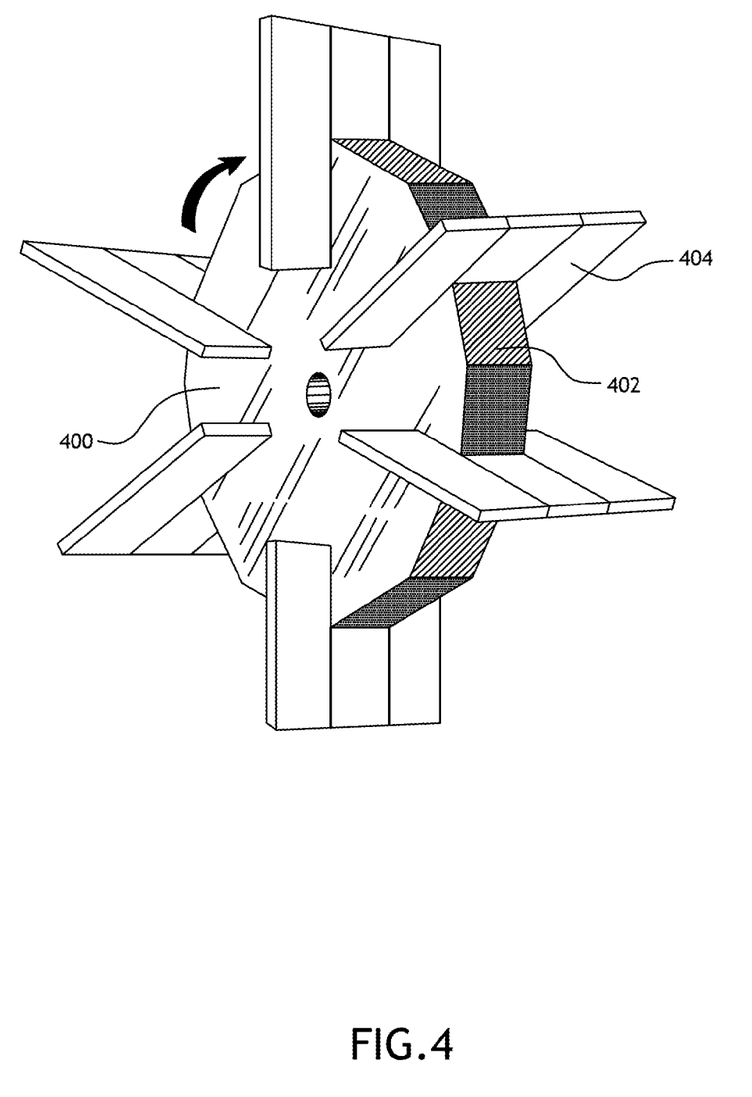
FIG. 4 is an isometric view of an illumination system including a particle deflecting structure.

Referring to FIG. 4, another embodiment of the illumination system in accordance with the present disclosure is shown. The illumination system may also include a particle deflecting structure including a plurality of vanes 404 attached to the base member 400. The vanes 404 are configured for deflecting particles which may be created by the illumination sources during their operation away from the mirrors 402. The particles may be comprised of material near the illumination source and material removed by energetic species produced coincidentally during light generation. The particles can range in size from atoms to micron-sized dust. These particles can collect on the mirrors 402 and reduce the reflectance of the mirrors 402, alter the surface of the mirrors 402 by striking them and roughening them, or bounce off the mirrors 402 and into other parts of the illumination system. The vanes 404 are therefore used to deflect the particles so that they do not strike the surface of the mirrors 402, and so the particles are not sent towards additional parts of the illumination system or nearby systems.

The vanes 404 are configured to avoid interference with the mirrors 402 receiving and reflecting the radiation from the illumination sources. The number and configuration of vanes 404 may vary depending on the rotation speed, number and configuration of illumination sources and their corresponding mirrors 402.

The vanes 404 may be sized and oriented around the base member 400 such that the pulsewidth of the light pulse from an illumination source has time to be reflected from the surface of one of the mirrors 402 before the next vane 404 in the rotation blocks the path of the light from the illumination source. For instance, the timing between two vanes 404 must be sufficient to satisfy a time that is twice the pulsewidth of an illumination source. In addition, the vanes 404 must be sized to intersect a particle that is travelling toward the mirrors 402.

The length and orientation of the vanes 404 may depend on the estimated velocity of the particles, the number of mirrors 402 and the rotation speed of the base member 404. In one embodiment, the vanes 404 may include apertures. Further, the angle of the vanes 404 may vary to direct the particles to a desired location, and also facilitate a clear path for the light to contact the mirrors 402 and be reflected by the mirrors 402 to the common optical path.

In one example, if the base member 400 includes 6 vanes 404, has a diameter of 10 centimeters, and rotates at 20,000 rpm, the edge of the base member will have a speed of over 100 meters per second. This velocity is sufficient to cause damage to the mirrors 402 if particles enter the system and come into contact with the mirrors 402. In this example, the particles may have a velocity of 100 meters per second, and the time between vanes 404 is equal to 500 microseconds. The vanes 404 will need to be approximately 5 centimeters long so that a particle may not traverse this distance without striking one of the vanes 404. As an additional example, if the base member 400 has a lower rotation speed resulting in a particle speed of 35 meters per second, the vanes 404 may be dimensioned smaller at approximately 2 cm long.

Figure 5:
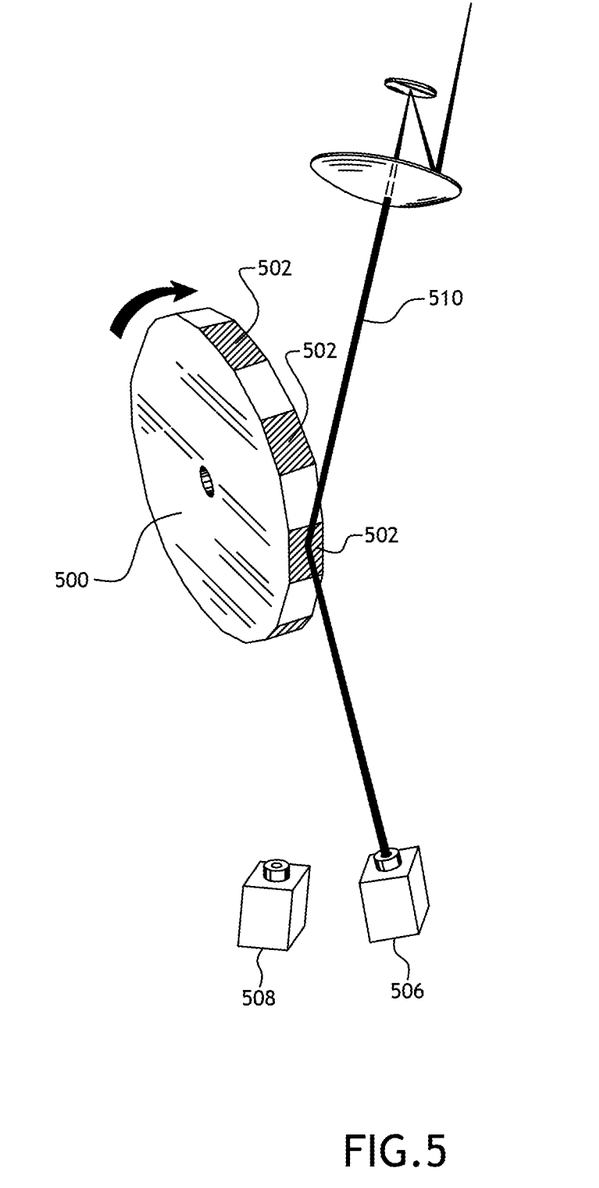
FIG. 5 is an isometric view of an illumination system having an alternative axis of rotation.

Referring to FIG. 5, another embodiment of the illumination system in accordance with the present disclosure is presented. The orientation of the illumination system may be varied relative to the illumination sources and common optical path.

The illumination system may further comprise a position sensor configured for monitoring the speed uniformity across the mirrors at more than one location. In one embodiment, the position sensor consists of an LED light shining onto a mirror. The light is reflected from the mirror into a detector. The position sensor may be used to monitor the speed uniformity at multiple locations on the mirror, providing feedback about the rate of rotation of the base member.

The illumination system may further include a field stop/aperture and a pupil stop/aperture, which may be placed on the optical path to improve the illumination stability. In a Kohler illumination scheme, source emission is collected by some kinds of collector (ellipsoid mirror, or Wolter-type mirror) to form an image. The image of source is designed as the entrance pupil of a condenser (for example Schwarzschild or Equal-Radii), which is used to focus light, while maintaining good illumination telecentricity. The field stop is a conjugate of the illumination field and the field and pupil stops determine the optical path. Due to source pulse length and timing jitter, movable mirror wobble and vibration, base member velocity instability, the light centroid after each mirror may deviate from the common optical path.

By placing the field and pupil stops after the mirrors on the optical path in accordance with the present disclosure, only a fixed portion out of the spread light is let through, resulting into more stable illumination. In addition, the field and pupil stops may also serve the purpose of define the location, size and shape of illumination pupil and field.

It is contemplated that configuring the base member as a cylindrical disc, as depicted in FIGS. 1 through 5, is merely exemplary. The base member may be configured in different ways to provide similar results. The specific shape of the base member may vary based on the number of light sources and corresponding mirrors. For instance, the base member referenced in the present disclosure may include a spherical or curved shape. Such a shape may be formed utilizing a plurality of segmented curved mirrors that correspond to the light sources.

The mirrors of the present disclosure may be configured for receiving light from the illumination sources at grazing incidence and reflecting the light to the optical path. The mirrors may also be configured for reflecting radiation at a normal incident to the mirror.

It is contemplated that the illumination sources in accordance with the present disclosure may also be utilized for other pulsed light sources in addition to EUV DPP or LPP sources. Other light sources may include, but are not limited to, infrared to ultraviolet laser, ultraviolet arc lamp, laser-enhanced ultraviolet plasma light source or the like. It is further contemplated that an individual illumination source may also be comprised of multiple illumination sources.

Additionally and/or alternatively, more than one of the illumination systems described in this disclosure may be utilized in a cascade manner to deliver EUV photons to the same location. That is, the output of one of the illumination systems may be utilized as the input/source for another illumination system. Such a cascade configuration may also improve both brightness and illumination uniformity.

Figure 6:
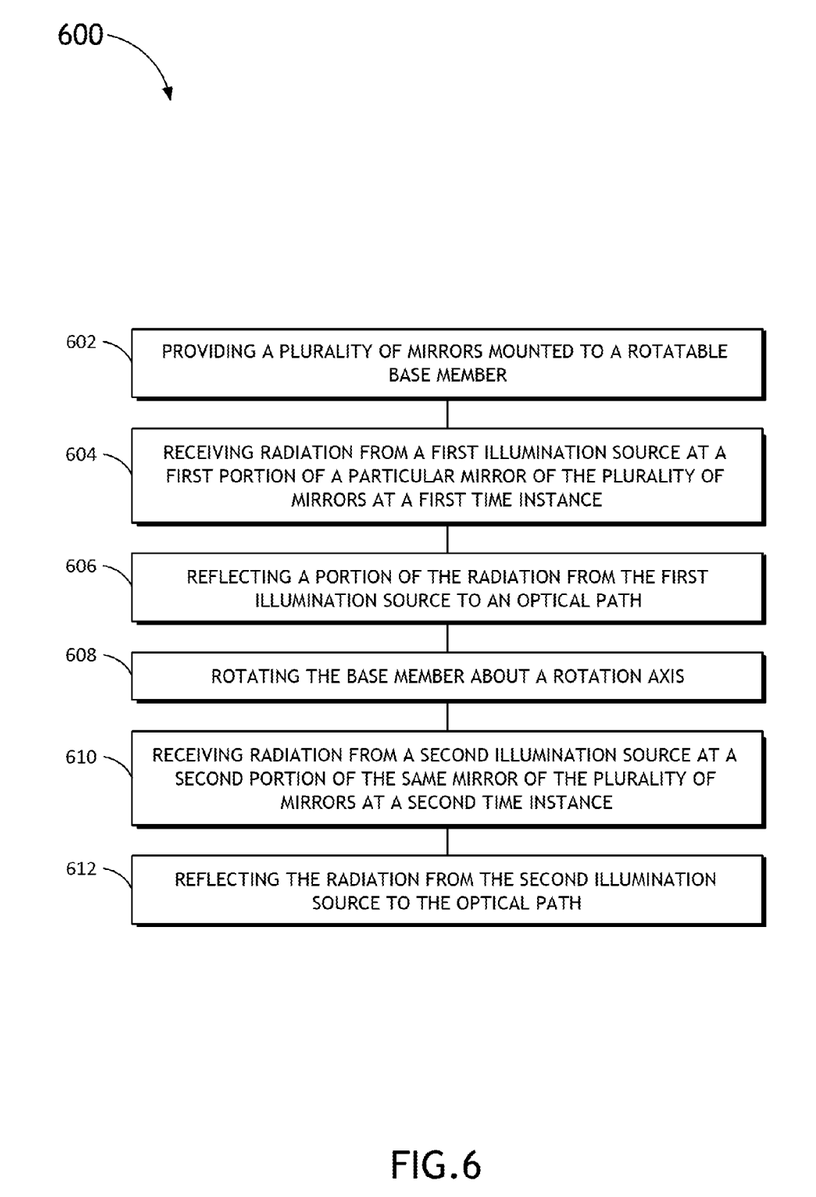
FIG. 6 is a flow diagram of a method for reflecting radiation from a plurality of illumination sources to a common optical path.

Referring to FIG. 6, a method 600 for reflecting radiation from a plurality of illumination sources to a common optical path is illustrated in accordance with the present disclosure. The method comprises the step of providing a plurality of mirrors mounted to a rotatable base member 602. The next step involves receiving radiation from a first illumination source at a first portion of a particular mirror of the plurality of mirrors at a first time instance 604. The radiation is reflected from the first illumination source to an optical path 606. The base member is then rotated about a rotation axis 608, and radiation from a second illumination source at a second portion of the same mirror of the plurality of mirrors at a second time instance are received 610. Finally, the radiation from the second illumination source is reflected to the same optical path 612.

Figure 7A:
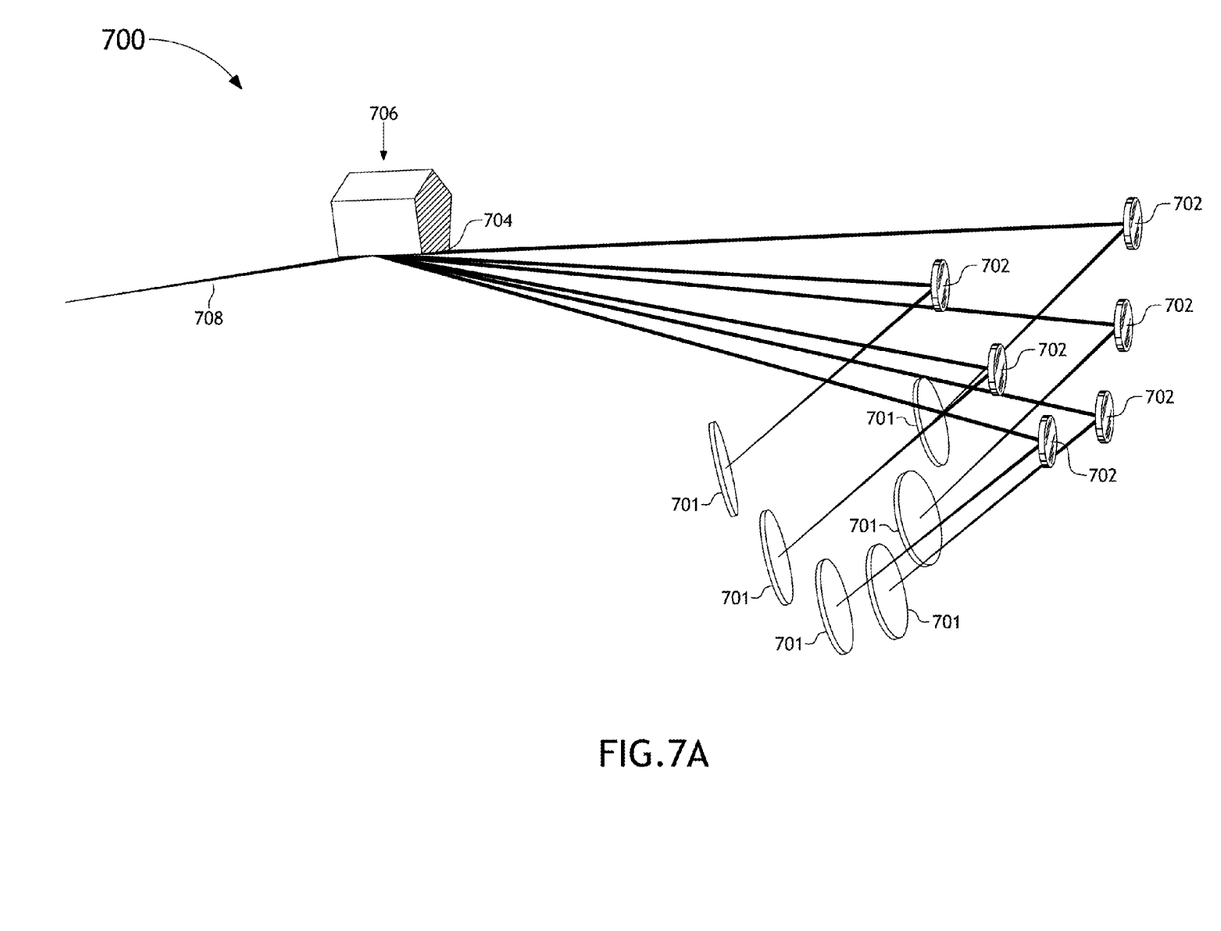
FIG. 7A is an isometric view of an illumination system including sources arranged in an arc configuration.

Referring to FIG. 7A, an additional embodiment of the illumination system 700 in accordance with the present disclosure is shown. The illumination system 700 in FIG. 7A shows how a plurality of illumination sources 701 may be arranged in an arc formation to strike the same face 704 of the base member 706 and divert the light to a common optical path 708. The plurality of illumination sources 701 may arranged to project radiation onto collector mirrors 702. The radiation travels from the illumination sources 701 to the collector mirrors 702, where it is reflected onto the face 704 of the base member 706. Additionally, FIG. 7B shows an alternative view of the illumination system 700.

Figure 7B:
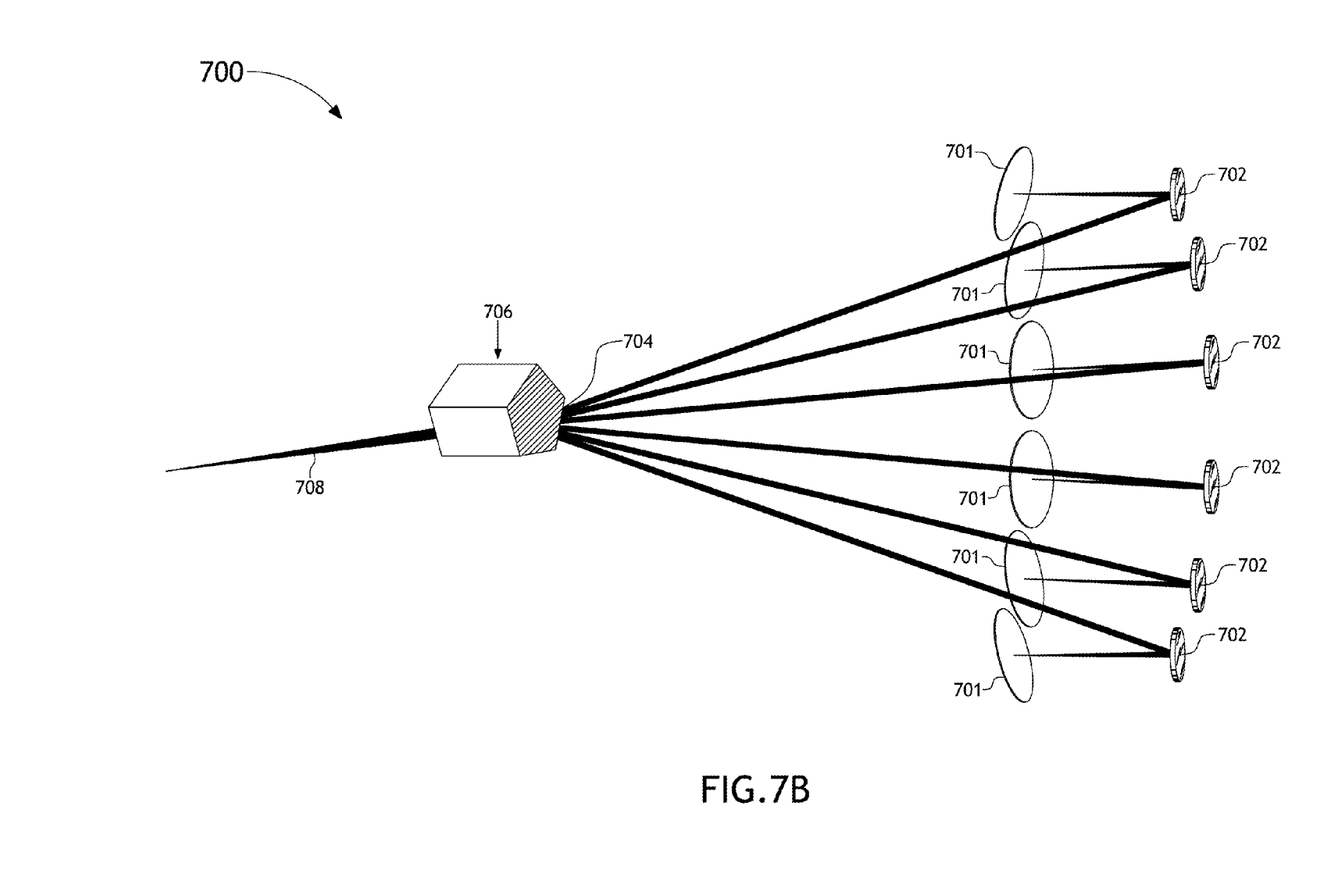
FIG. 7B is an alternative isometric view of an illumination system including sources arranged in the arc configuration.
Figure 8:
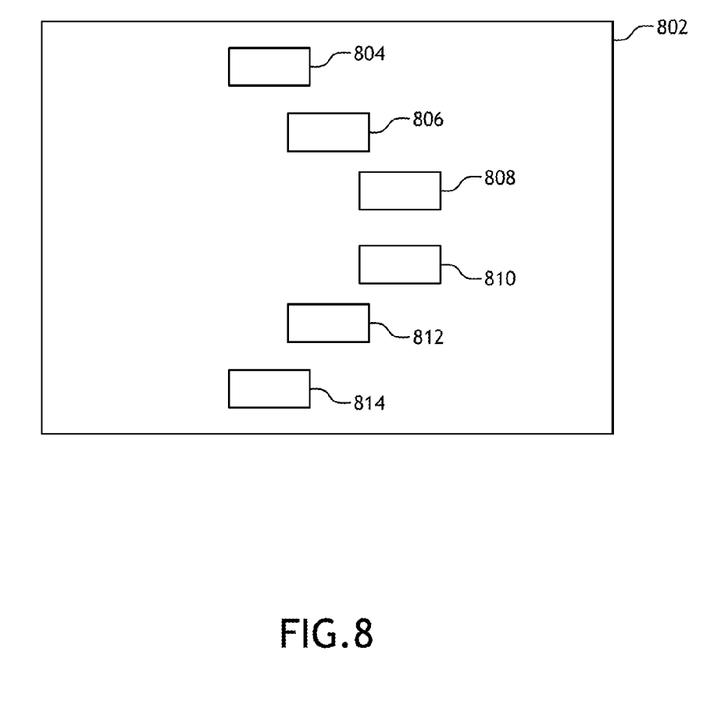
FIG. 8 depicts an exemplary mirror surface of one of the mirrors of the base member of FIGS. 7A and 7B.

In FIG. 8, an exemplary mirror surface 802 of one of the mirrors of the base member of FIGS. 7A and 7B is provided. The mirror surface 802 shows locations 804, 806, 808, 810, 812, 814 where each of a plurality of illumination sources arranged in an arc formation would contact the same mirror surface 802 at different locations 804-814. The exemplary mirror surface 802 shown in FIG. 8 may represent the locations 804-814 where the illumination sources arranged in the arc configuration of FIGS. 7A and 7B may contact the mirror surface 802.

The methods disclosed may be implemented as sets of instructions, through a single production device, and/or through multiple production devices. Further, it is understood that the specific order or hierarchy of steps in the methods disclosed are examples of exemplary approaches. Based upon design preferences, it is understood that the specific order or hierarchy of steps in the method can be rearranged while remaining within the scope and spirit of the disclosure. The accompanying method claims present elements of the various steps in a sample order, and are not necessarily meant to be limited to the specific order or hierarchy presented.

It is believed that the system and method of the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory.

What is claimed is:

1. An illumination system, comprising:
a base member rotatable about a rotation axis;
a first plurality of mirrors, each mirror of said first plurality of mirrors disposed on an outer surface of the base member along a perimeter of the base member and oriented at a predetermined angle;
a first illumination source; and
a second illumination source,
wherein a mirror of the first plurality of mirrors is configured to receive radiation from the first illumination source at a first portion of the mirror at a first time, the mirror is further configured to reflect the radiation to an optical path, the mirror is further configured to receive radiation from the second illumination source at a second portion of the mirror at a second time, the mirror further configured to reflect the radiation to the optical path, the first portion being different from the second portion.

2. The illumination system of claim 1, further comprising a third illumination source, fourth illumination source, fifth illumination source, and sixth illumination source, wherein the mirror of the first plurality of mirrors is configured to receive radiation from the third illumination source at a third portion of the mirror at a third time, the mirror is further configured to reflect the radiation to the optical path, the mirror is further configured to receive radiation from the fourth illumination source at a fourth portion of the mirror at a fourth time, the mirror further configured to reflect the radiation to the optical path, the mirror is further configured to receive radiation from the fifth illumination source at a fifth portion of the mirror at a fifth time, the mirror further configured to reflect the radiation to the optical path, the mirror is further configured to receive radiation from the sixth illumination source at a sixth portion of the mirror at a sixth time, the mirror further configured to reflect the radiation to the optical path.

3. The illumination system of claim 2, wherein the first illumination source, second illumination source, third illumination source, fourth illumination source, fifth illumination source, and sixth illumination source are arranged in an arc configuration.

4. The illumination system of claim 1, wherein each of the first illumination source and the second illumination source is a pulsed EUV source.

5. The illumination system of claim 1, wherein each of the first illumination source and the second illumination source is a plurality of pulsed EUV sources.

6. The illumination system of claim 1, wherein the base member is configured for rotating at a predetermined speed, the predetermined speed corresponding to the degree of rotation required to enable each mirror of the plurality of mirrors to receive radiation from the first illumination source at a first portion of the mirror at a first time and reflect the radiation to an optical path and for the same mirror of the plurality of mirrors to receive radiation from the second illumination source at the second portion at the second instance and reflect the radiation to the optical path.

7. The illumination system of claim 1, further comprising a position sensor configured for monitoring the speed uniformity across a mirror of the first plurality of mirrors at a plurality of locations.

8. The illumination system of claim 1, further comprising a particle deflecting structure attached to the base member, the particle deflecting structure configured for deflecting particles.

9. The illumination system of claim 1, wherein the plurality of mirrors is configured for reflecting radiation from the first illumination source and the second illumination source at grazing incidence.

10. The illumination system of claim 1, wherein the plurality of mirrors is configured for reflecting radiation from the first illumination source and the second illumination source at near-normal incidence.

11. The illumination system of claim 1, further comprising:
a second plurality of mirrors, each mirror of said second plurality of mirrors disposed on an outer surface of the base member along a perimeter of the base member and oriented at a second predetermined angle;
a third illumination source; and
a fourth illumination source;
wherein each of the second plurality of mirrors is interleaved with the first plurality of mirrors, and a mirror of the second plurality of mirrors is configured for receiving radiation from the third illumination source at a first portion of the mirror at a third time and reflecting the radiation to an optical path and the same mirror of the second plurality of mirrors is configured for receiving radiation from the fourth illumination source at a second portion of the mirror at a fourth time and reflecting the radiation to the optical path, the first portion being different from the second portion.

12. An illumination system, comprising:
a base member rotatable about a rotation axis;
a first plurality of mirrors, each mirror of said first plurality of mirrors disposed on an outer surface of the base member along a perimeter of the base member and oriented at a predetermined angle;
a second plurality of mirrors, each mirror of said second plurality of mirrors disposed on an outer surface of the base member along a perimeter of the base member and oriented at a second predetermined angle;
a first illumination source, and
a second illumination source;
a third illumination source; and
a fourth illumination source;
wherein each mirror of the first plurality of mirrors is interleaved with each mirror of the second plurality of mirrors, a mirror of the first plurality of mirrors is configured for receiving radiation from the first illumination source at a first portion of the mirror at a first time and reflecting the radiation to an optical path and the same mirror of the first plurality of mirrors is configured for receiving radiation from the second illumination source at a second portion of the mirror at a second time and reflecting the radiation to the optical path, the first portion being different from the second portion, and a mirror of the second plurality of mirrors is configured for receiving radiation from the third illumination source at a first portion of the mirror at a third time and reflecting the radiation to an optical path and the same mirror of the second plurality of mirrors is configured for receiving radiation from the fourth illumination source at a second portion of the mirror at a fourth time and reflecting the radiation to the optical path, the first portion being different from the second portion.

13. The illumination system of claim 12, wherein each of the first, second, third and fourth illumination sources is a pulsed EUV source.

14. The illumination system of claim 12, wherein the base member is configured for rotating at a predetermined speed, the predetermined speed corresponding to the degree of rotation required to enable each mirror of the first plurality of mirrors and the second plurality of mirrors to receive radiation and reflect the radiation to the optical path.

15. The illumination system of claim 12, further comprising a position sensor configured for monitoring the speed uniformity across a mirror of the first plurality of mirrors or the second plurality of mirrors at a plurality of locations.

16. The illumination system of claim 12, further comprising a particle deflecting structure attached to the base member, the particle deflecting structure configured for deflecting particles.

17. The illumination system of claim 12, wherein at least one of the first plurality of mirrors and the second plurality of mirrors is configured for reflecting radiation at grazing incidence.

18. The illumination system of claim 12, wherein at least one of the first plurality of mirrors and the second plurality of mirrors is configured for reflecting radiation at near-normal incidence.

19. The illumination system of claim 12, wherein the first illumination source, second illumination source, third illumination source, and fourth illumination source are arranged in an arc configuration.

* * * * *